United States Patent
Ueminami et al.

(10) Patent No.: US 9,655,788 B2
(45) Date of Patent: *May 23, 2017

(54) ABSORBENT ARTICLE HAVING TRAVERSE REINFORCING ELEMENT

(71) Applicant: The Procter & Gamble Company, Cincinnati, OH (US)

(72) Inventors: Atsushi Ueminami, Kobe (JP); Maki Hasegawa, Suita (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/516,847

(22) Filed: Oct. 17, 2014

(65) Prior Publication Data

US 2015/0038932 A1    Feb. 5, 2015

Related U.S. Application Data

(63) Continuation of application No. 13/919,190, filed on Jun. 13, 2013, now Pat. No. 8,878,000, which is a (Continued)

(51) Int. Cl.
*A61F 13/15* (2006.01)
*A61F 13/20* (2006.01)
(Continued)

(52) U.S. Cl.
CPC ...... *A61F 13/4702* (2013.01); *A61F 13/4704* (2013.01); *A61F 13/4756* (2013.01); *A61F 13/4758* (2013.01); *A61F 13/533* (2013.01)

(58) Field of Classification Search
CPC .............. A61F 13/4702; A61F 13/4704; A61F 13/4756; A61F 13/533
(Continued)

(56) References Cited

U.S. PATENT DOCUMENTS 3,575,174 A    4/1971  Mogor
4,397,644 A    8/1983  Matthews et al.
(Continued)

FOREIGN PATENT DOCUMENTS

EP    0 304 957 B2    4/1994
EP    0 597 273 A1    5/1994
(Continued)

OTHER PUBLICATIONS

PCT International Search Report dated Apr. 9, 2006.

*Primary Examiner* — Michele M Kidwell
(74) *Attorney, Agent, or Firm* — Andres E. Velarde (57) ABSTRACT

An absorbent article having a front end region, a rear end region, a central region disposed between the front and rear end regions, a fluids source area, and a transverse axis and a longitudinal axis. The absorbent article includes a topsheet, a backsheet, an absorbent core disposed between the topsheet and the backsheet, and a reinforcing structure disposed within the central region. In one aspect of the invention, the reinforcing structure includes a pair of traverse reinforcing elements each of which is formed by two traverse channels. The two traverse channels may be disposed generally parallel to the transverse axis with a reinforcement distance such that the absorbent core has an average density of in the range of about 5% to about 500% higher at the traverse reinforcing element than the fluids source area.

10 Claims, 3 Drawing Sheets

Related U.S. Application Data continuation of application No. 11/443,708, filed on May 31, 2006, now Pat. No. 8,481,806.

(60) Provisional application No. 60/686,814, filed on Jun. 2, 2005.

(51) Int. Cl.
*A61F 13/47* (2006.01)
*A61F 13/475* (2006.01)
*A61F 13/533* (2006.01)

(58) Field of Classification Search
USPC .......... 604/378–383, 385.01, 385.24, 385.27
See application file for complete search history.

(56) References Cited

U.S. PATENT DOCUMENTS

| | | | |
|---|---|---|---|
| 4,624,666 A | 11/1986 | DeRossett et al. | |
| 4,655,759 A | 4/1987 | Romans-Hess et al. | |
| 4,773,905 A | 9/1988 | Molee et al. | |
| 4,886,513 A | 12/1989 | Mason, Jr. et al. | |
| 4,936,839 A | 6/1990 | Molee et al. | |
| 5,092,860 A | 3/1992 | Pigneul | |
| 5,399,175 A | 3/1995 | Glaug et al. | |
| 5,447,506 A | 9/1995 | Lindquist | |
| 5,795,344 A | 8/1998 | Chappell | |
| 5,795,345 A | 8/1998 | Mizutani et al. | |
| 5,807,365 A | 9/1998 | Luceri | |
| 5,981,824 A | 11/1999 | Luceri | |
| 6,506,959 B2 | 1/2003 | Hamajima et al. | |
| 6,617,490 B1 | 9/2003 | Chen et al. | |
| 6,764,477 B1 | 7/2004 | Chen et al. | |
| 7,037,298 B2 | 5/2006 | Ohshima et al. | |
| 7,312,372 B2 | 12/2007 | Miyama et al. | |
| 2004/0243082 A1 | 12/2004 | Kinoshita et al. | |
| 2005/0148972 A1 | 7/2005 | Miyama et al. | |
| 2005/0148973 A1 | 7/2005 | Tamura et al. | |

FOREIGN PATENT DOCUMENTS

| | | |
|---|---|---|
| EP | 0 360 680 B1 | 11/1994 |
| EP | 0 597 273 B1 | 6/1998 |
| EP | 1 332 742 A1 | 8/2003 |
| EP | 0 852 938 B1 | 3/2005 |
| GB | 2 319 730 A | 6/1998 |
| GB | 2 354 449 A | 3/2001 |
| JP | 05-086320 | 4/1993 |
| JP | 10-272155 | 10/1998 |
| JP | 11-189961 | 7/1999 |
| JP | 11-299821 | 11/1999 |
| JP | 2001-017467 | 1/2001 |
| JP | 2003-284742 | 10/2003 |
| JP | 2004-113538 | 4/2004 |
| WO | WO 9724092 A1 | 7/1997 |
| WO | WO 9827908 A1 | 7/1998 |
| WO | WO 0032145 A1 | 8/2000 |
| WO | WO 2004-021947 | 3/2004 |

ABSORBENT ARTICLE HAVING TRAVERSE REINFORCING ELEMENT

FIELD OF THE INVENTION

The present invention relates to absorbent articles such as sanitary napkins, pantiliners, and incontinence pads. More particularly, the present invention relates to absorbent articles having traverse reinforcing elements.

BACKGROUND OF THE INVENTION

Absorbent articles, such as sanitary napkins, pantiliners, and incontinence pads, are typically worn in the crotch region of an undergarment. These devices are designed to absorb and retain liquids and other discharges from the human body to prevent body and garment soiling. The aforementioned types of absorbent articles are typically placed in a garment such as the wearer's panty and worn between the wearer's legs, adjacent to the genital (or fluids discharge source) area of the body.

Conventional relatively thick sanitary napkin products currently marketed provide some protection from soiling by utilizing a combination of increased product length and thickness (which may include a profiled or varied caliper). These products, however, are not believed to prevent leakage of body fluids perfectly in particular when the sanitary napkin is compressed by a strong compressive force which is sometimes applied by the body of the wearer when the absorbent article is worn. Thus, leakage is possible, particularly at the both sides of the central region, and sometimes at the front and/or rear regions of these products. This issue is seen not only in conventional relatively thick sanitary napkin products but also other conventional products such as relatively thinner and smaller sanitary napkins as well as other types of absorbent articles, e.g., pantiliners, diapers, and incontinence pads in the market.

Thus, there is a need for an absorbent article that provides improved leakage protection of body fluids. There is another need for an absorbent article having a structure that can produce a sustainable force against a compressive force which is applied by the body of the wearer when the absorbent article is worn.

SUMMARY OF THE INVENTION

The invention is directed to an absorbent article having a front end region, a rear end region, a central region including a fluids source area, the central region disposed between the front and rear end regions, and a transverse axis and a longitudinal axis. The absorbent article includes: a topsheet; a backsheet; an absorbent core disposed between the topsheet and the backsheet; and a reinforcing structure disposed within the central region.

In one aspect of the invention, the reinforcing structure includes a pair of traverse reinforcing elements each of which is formed by two traverse channels. The two traverse channels are disposed generally parallel to the transverse axis with a reinforcement distance such that the absorbent core has an average density in the range of about 5 to about 500% higher at the traverse reinforcing element than the fluids source area.

In another aspect of the invention, the reinforcing structure includes at least one traverse reinforcing element which is formed by two traverse channels. The two channels are disposed generally parallel to the transverse axis with a reinforcement distance such that the at least one traverse reinforcing element has a compressive modulus in the range of about 8 to about 30 psi (in the range of about 55.2 to about 206.8 kPa).

The foregoing may provide improved leakage protection of body fluids. The foregoing may also provide an absorbent article having a structure that can produce a sustainable force against a compressive force which is applied by the body of the wearer when the absorbent article is worn.

These and other features, aspects, and advantages of the present invention will become evident to those skilled in the art from reading of the present disclosure.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

DETAILED DESCRIPTION OF THE INVENTION

Herein, "comprise" and "include" mean that other elements and/or other steps which do not affect the end result can be added. Each of these terms encompasses the terms "consisting of" and "consisting essentially of".

Herein, "absorbent article" refers to articles which absorb and contain body exudates or discharges such as body fluids, and is intended to include sanitary napkins, pantiliners, diapers, and incontinence pads (and other articles worn in the crotch region of a garment) as well as diapers, training pants and pull-on diapers, briefs and the like.

Herein, "disposable article" refers to articles which are intended to be discarded after a single use, composted, or otherwise disposed of in an environmentally compatible manner. (That is, they are not intended to be laundered or otherwise restored or reused as an absorbent article.)

Herein, "sanitary napkin" refers to articles which are worn by females adjacent to the pudendal region which are intended to absorb and contain the various exudates which are discharged from the body (e.g., blood, menses, and urine). It should be understood, however, that the present invention is also applicable to other hygiene pads such as pantiliners, diapers, and incontinence pads worn in the crotch region of a garment.

Herein, "joined" encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element.

Herein, "body surface" refers to surfaces of absorbent articles and/or their component members which face the body of the wearer, while "garment surface" refers to the opposite surfaces of the absorbent articles and/or their component members that face away from the wearer when the absorbent articles are worn. Absorbent articles and components thereof, including the topsheet, backsheet, absorbent core, and any individual layers of their components, have a body surface and a garment surface.

Herein, "fluids source area" refers to a part of specific area of the body surface of absorbent articles where the source of body fluids of the wearer is expected to come most closely when the absorbent article is worn.

Herein, "longitudinal" refers to a line, axis or direction in the plane of an absorbent article that is generally aligned with (e.g., approximately parallel to) a vertical plane which bisects a standing wearer into left and right body halves when the absorbent article is worn. Herein, "longitudinal axis" refers to a longitudinal axis that bisects the body surface of absorbent articles symmetrically along the line.

Herein, "transverse" or "lateral" refers to a line, axis or direction which lies within the plane of absorbent articles that is generally perpendicular to the longitudinal direction. Herein, "transverse axis" refers to a transverse axis that intersects the longitudinal axis at the center of the fluids source area.

Figure 1:
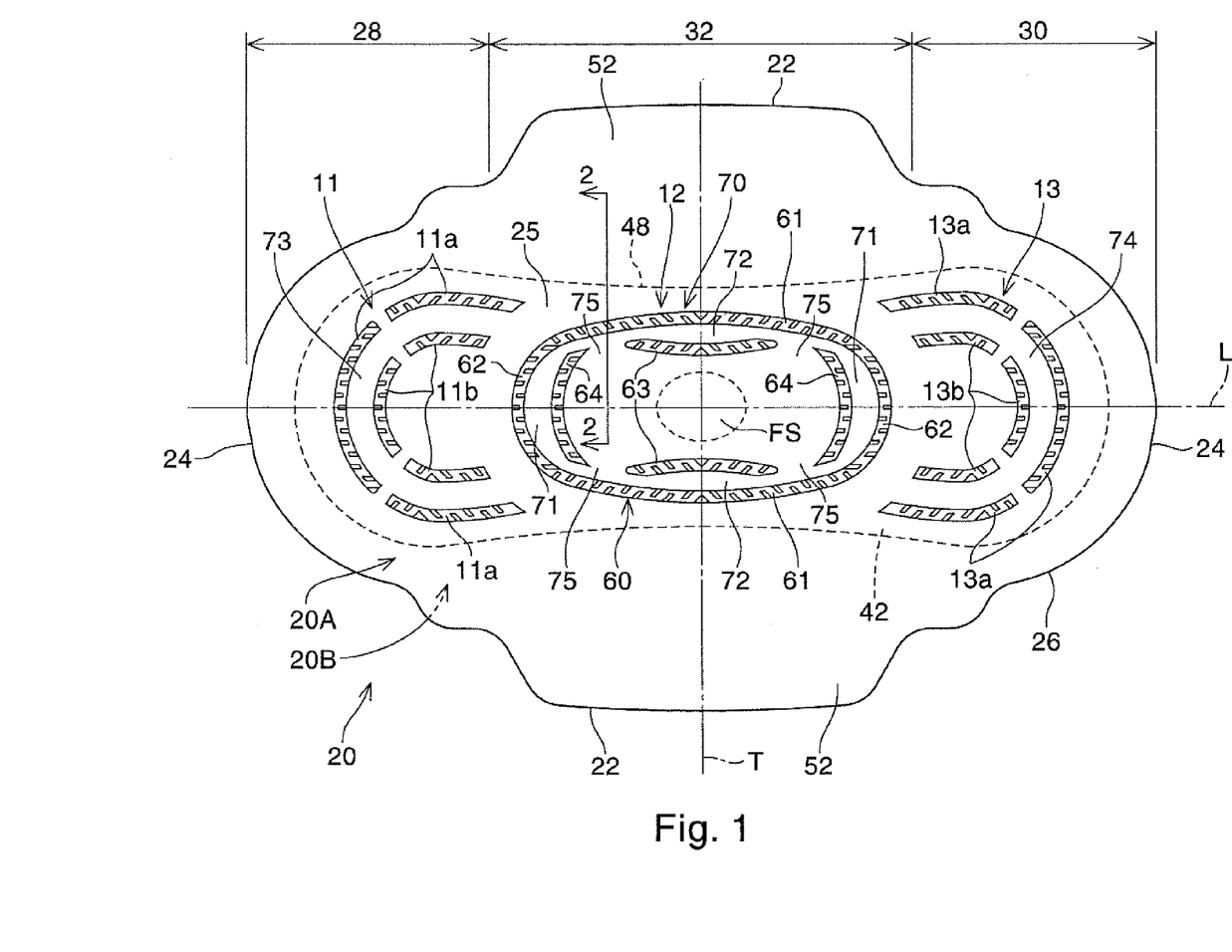
FIG. 1 is a top plane view of a preferred embodiment of the absorbent article of the present invention.

FIG. 1 is a top plane view of one embodiment of the absorbent article of the present invention. In the embodiments shown in FIGS. 1-5, the absorbent article is a relatively thick disposable sanitary napkin 20.

The sanitary napkin 20 has two surfaces, a liquid pervious body surface (or body-contacting surface) 20A and a liquid impervious garment surface 20B. The body surface 20A is intended to be worn adjacent to the body of the wearer. The garment surface 20B of the sanitary napkin 20 is on the opposite side and is intended to be placed adjacent to the wearer's undergarments when the sanitary napkin 20 is worn.

Referring to FIG. 1, the sanitary napkin 20 has a longitudinal axis L and a transverse axis T. The longitudinal axis L intersects the transverse axis T at the center of the fluids source area FS. The sanitary napkin 20 has two spaced apart longitudinal edges 22 and two spaced apart transverse or end edges 24, which jointly form the periphery 26 of the sanitary napkin 20. The sanitary napkin 20 also has two end regions, i.e., a front end region 28 and a rear end region 30. A central region 32 is disposed between the end regions 28 and 30. The sanitary napkin 20 includes a pair of central side flaps 52 in the central region 32. Each flap 52 extends laterally outward from a main body portion 25 in the central region 32.

The front end region 28 is defined as the area that is placed to the front of the wearer's body when the sanitary napkin 20 is worn. The rear end region 30 is defined as the area that is placed to the rear of the wearer's body. The central region 32 is defined as the area that is generally located directly below the perineum of the wearer and includes the fluids source area FS which typically receives the greatest amount of menses or other fluids from the wearer.

In one embodiment, each region can be defined with respect to the position of the fluids source area FS. Specifically, the central region 32 ends at a longitudinal distance which is selected from a range of about 30 to about 105 mm, or from a range of about 50 to about 70 mm from the center of the fluids source area FS. In the embodiment shown in FIG. 1, the central region 32 ends at a longitudinal distance of about 58 mm. In other words, each of the front and rear end regions 28 and 30 starts at that longitudinal distance from the center of the fluids source area FS, respectively.

Figure 2:
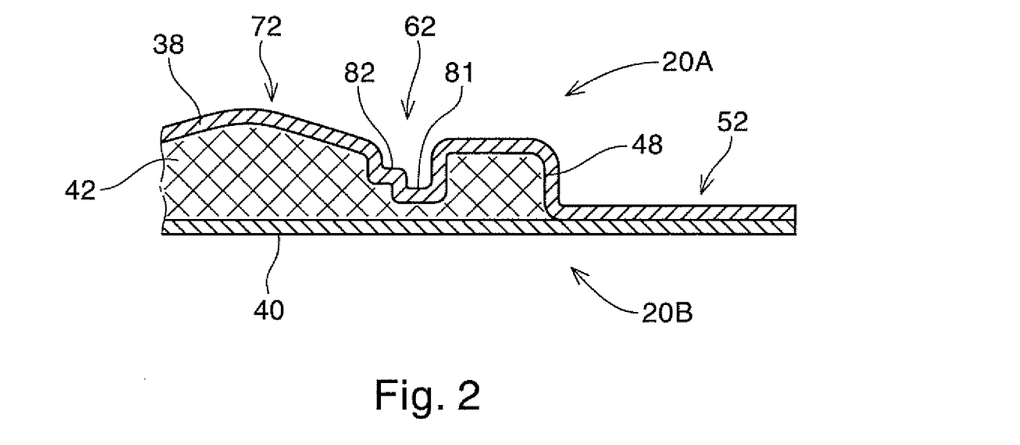
FIG. 2 is a schematic cross-sectional view of the absorbent article shown in FIG. 1 taken along line 2-2 of FIG. 1.

FIG. 2 is a cross-sectional view of the sanitary napkin 20 taken along the section line 2-2 in FIG. 1, which shows the individual components of the sanitary napkin 20 shown in FIG. 1. The sanitary napkin 20 shown in FIG. 2 generally comprises at least three primary components, i.e., a topsheet 38; a backsheet 40; an absorbent core 42 having longitudinal edges 48 disposed between the topsheet 38 and the backsheet 40. The central side flaps 52 extend laterally outward from the corresponding longitudinal edge 48 of the absorbent core 42 in the central region 32. The topsheet 38, backsheet 40, and absorbent core 42 can comprise any types of materials known in the art as being suitable for such components.

Referring again to FIG. 1, the sanitary napkin 20 includes central channels 12 formed in the central region 32. The central channels 12 may include an oval channel 60 which includes a pair of outwardly convex longitudinal channels 61 and a pair of outwardly convex traverse channels 62. Herein, "outwardly convex" means a specified channel has a curved line shape (including a polygonal lines shape) which is outwardly extended when looking from the longitudinal or traverse axis L or T. The central channels 12 may also include, within the area surrounded by the oval channels 60, a pair of inwardly convex longitudinal channels 63 and a pair of outwardly convex traverse channels 64. Herein, "inwardly convex" means a specified channel has a curved line shape (including a polygonal lines shape) which is inwardly extended when looking from the longitudinal or traverse axis L or T. The design of the central channels 12 including the total number thereof, and the length and shape of each component channel can vary depending on the design of the sanitary napkin 20.

The oval channel 60 can take any oval like shapes which include, for example, an actual oval shape defined by mathematics and an eye shape (i.e., a shape formed by two arc like lines), and the like. In the embodiment shown in FIG. 1, the oval channel 60 includes the pair of outwardly convex longitudinal channels 61 and the pair of outwardly convex traverse channels 62. The oval channel in the embodiment shown 60 has a maximum length of between about 25 and about 205 mm and a maximum width of between about 10 and about 75 mm. (Herein, the maximum length and the maximum width of the oval channel 60 are measured on the longitudinal axis L and the traverse axis T, respectively.) The oval channel 60 may have a maximum length of between about 60 and about 150 mm and a maximum width of between about 35 and about 55 mm. In the embodiment shown in FIG. 1, the oval channel 60 has a maximum length of about 96 mm and a maximum width of about 48 mm.

The oval channel 60 is not always necessary but generally desired since it forms a generally closed area defined by the channel structure in the central region 32 that can contribute to retain body fluids absorbed by the absorbent core 42 within the area.

Referring again to FIG. 1, the sanitary napkin 20 may include a reinforcing structure 70 disposed within the central region 32. The reinforcing structure 70 of the present invention may include at least one traverse reinforcing element 71 which is formed by at least two traverse channels 62 and 64. The two channels 62 and 64 are disposed generally parallel to the transverse axis T with a reinforcement distance RD such that the traverse reinforcing element has a compressive modulus of between about 8 and about 30 psi (between about 55.2 and about 206.8 kPa), or between about 10 and about 20 psi (between about 68.9 and about 137.9 kPa). Herein, "compressive modulus" is defined as a rate of a pressure kPa (kilopascal) required to cause a unit strain when a sample member is continuously pushed down at 75% of the original thickness (i.e., at a strain of 25%). The compressive modulus at a specified portion of an absorbent article correlates to the stiffness at the specified portion in both the parallel and perpendicular to the body surface 20A, and thus the sustainable force to be produced against a compressive force which is applied externally. For example, if a specified portion of an absorbent article has a higher compressive modulus than the other portion, the specified portion can produce a higher sustainable force against a compressive force applied externally. A suitable test method for measuring the compressive modulus of an absorbent article is disclosed hereinafter in the "TEST METHOD" section.

Herein, "reinforcing element" is a partial component of an absorbent article that has a higher stiffness than its surrounding portion(s). The reinforcing element is formed by two channels that are generally parallel. To form an effective reinforcing element, the two channels are disposed generally in parallel with a reinforcement distance. Herein, "reinforcement distance" is an average distance of two channels which can produce a compressive modulus that is higher than its surrounding portion(s) of the absorbent article. Herein, "distance" of two generally long components is measured as the interval between two corresponding points of the two components in the longitudinal or traverse direction.

In one embodiment, the reinforcement distance of the two channels is selected such that the absorbent core has an average density which is higher at the traverse reinforcing element than the other un-compressed (or un-embossed) area. Herein, average densities of an absorbent core are calculated by a caliper which is measured under the pressure of 0.049 kPa by using a circular comparator foot having an area of about 2 cm$^2$.

The reinforcement distance of the two channels is selected such that the reinforcing element can produce enough sustainable force required at the portion(s) in the absorbent article. The two channels which form the reinforcing element have a reinforcement distance of between about 1 and about 40 mm, between about 2 and about 20 mm, or between about 4 and about 8 mm. As a result, the reinforcing element is generally stiffer than its surrounding portion(s) of the absorbent article such that it can produce a sustainable force against a compressive force which is applied by the body of the wearer when the absorbent article is worn.

The reinforcing structure 70 shown in FIG. 1 includes a pair of traverse reinforcing elements 71 formed by the four traverse channels 62 and 64. In one embodiment, the reinforcement distance of the two channels is selected such that the absorbent core 42 has an average density of between about 5 and about 500%, between about 20 and about 100%, or between about 30 and about 60% higher at the reinforcing element than that of the fluids source area FS. The reinforcement distance of the two traverse channels 62 and 64 may be selected such that the traverse reinforcing element 71 has a compressive modulus which is higher than that of the fluids source area FS. The reinforcement distance of the two traverse channels 62 and 64 may be selected such that the traverse reinforcing element 71 has a compressive modulus of between about 2 and about 50 psi (between about 13.8 and about 344.7 kPa), or between about 8 and about 30 psi (between about 55.2 and about 206.8 kPa), or between about 10 and about 20 psi (between about 68.9 and about 137.9 kPa).

Such higher compressive modulus at the reinforcing elements 71 is brought by higher density of the absorbent core material at the reinforcing elements 71 which is caused by the formation of the traverse channels 62 and 64. For example, in the embodiment of FIG. 1, the absorbent core 42 includes 100 weight % of cellulose fibers which have an average density of between about 5 and about 500%, between about 20 and about 100%, or between about 30 and about 60% higher at the traverse reinforcing elements 71 than the fluids source area FS.

The longitudinal distance of the traverse reinforcing elements 71 is decided depending on the design of the sanitary napkin 20. The pair of the traverse reinforcing elements 71 are generally disposed with a longitudinal distance of between about 20 and about 110 mm on the longitudinal axis, between about 50 and about 100 mm, or between about 80 and about 90 mm. Herein, the longitudinal distance of the traverse reinforcing elements 71 is measured between the center positions of each traverse reinforcing element 71 on the longitudinal axis L.

The traverse length of the traverse reinforcing elements 71 is also decided depending on the design of the sanitary napkin 20. The traverse reinforcing elements 71 may have a traverse length of between about 20% and about 100%, between about 30% and about 70%, or between about 40% and about 50% of the minimum width of the absorbent core 42. (The width of the absorbent core 42 is defined by the traverse distance between the longitudinal edges 48 of the absorbent core 42.)

The total number and the lengths of the channels 62 and 64 which form the reinforcing structure 70 (i.e., the reinforcing elements) can vary depending on the design of the sanitary napkin 20. In one embodiment, the sanitary napkin 20 includes only two traverse channels which form only one reinforcing element that is typically disposed on the traverse axis T.

The sanitary napkin 20 may include at least one longitudinal channel extending in a direction generally parallel to the longitudinal axis L. In one embodiment, the sanitary napkin 20 includes only one longitudinal channel which is typically disposed on the longitudinal axis L. The total number may be at least two, wherein one longitudinal channel is disposed symmetrically on either side of the longitudinal axis L.

Referring again to FIG. 1, the sanitary napkin 20 includes four longitudinal channels extending in a direction generally parallel to the longitudinal axis L, i.e., the pair of longitudinal channels 61 and the pair of longitudinal channels 63. These longitudinal channels 61 and 63 are disposed symmetrically on either side of the longitudinal axis L.

The reinforcing structure 70 can include an additional reinforcing element(s) in both the longitudinal and traverse direction(s). Such additional reinforcing element(s) can be disposed any region 28, 30, 32 but are generally within the central region 32. In one embodiment, the reinforcing structure includes at least one longitudinal reinforcing element which is formed by two longitudinal channels. In the embodiment shown in FIG. 1, the reinforcing structure 70 includes a pair of longitudinal reinforcing elements 72 each of which is formed by the two longitudinal channels 61 and 63. The two longitudinal channels 61 and 63 are disposed generally parallel to the longitudinal axis L with a reinforcement distance such that the absorbent core 42 has an average density in the range of about 5 to about 500%, in the range of about 20 to about 100%, or in the range of about 30 to about 60% higher at the traverse reinforcing element than that of the fluids source area FS. The reinforcement distance of the two longitudinal channels 61 and 63 may be selected such that the longitudinal reinforcing element has a compressive modulus of in the range of about 2 to about 50 psi (in the range of about 13.8 to about 344.7 kPa), or in the range of about 8 to about 30 psi (in the range of about 55.2 to about 206.8 kPa), or in the range of about 10 to about 20 psi (in the range of about 68.9 to about 137.9 kPa).

In the embodiment shown in FIG. 1, the pair of traverse reinforcing elements 71 and the pair of longitudinal reinforcing elements 72 are separated by non-reinforcing element portions 75 (in other words, they are connected by the non-channel portions 75). If desired, however, the pair of traverse reinforcing elements 71 and the pair of longitudinal reinforcing elements 72 can be connected by reinforcing element portions.

Referring again to FIG. 1, the sanitary napkin 20 includes front channels 11 formed in the front end region 28, and rear channels 13 formed in the rear end region 30. The front channels 11 include two outwardly convex arc channels 11a and 11b, while the rear channels 13 include two outwardly convex arc channels 13a and 13b. It should be noted that the front channels 11 and the rear channels 13 are optional, but they can be especially beneficial when they also provide an outwardly convex arc like reinforcing element 73, 74 in each region 28 and 30 as shown in FIG. 1. For example, the sanitary napkin 20 further includes the outwardly convex arc like reinforcing element 73 which is formed by the two arc channels 11a and 11b formed in the front end region 28, and the outwardly convex arc like reinforcing element 74 which is formed by the two arc channels 13a and 13b formed in the rear end region 30. These arc like reinforcing elements 73 and 74 also produce a sustainable force against a compressive force which may be applied in each region 28, 30 by the body of the wearer when the absorbent article is worn. In addition, since each of the arc like reinforcing elements 73 and 74 may be provided with a higher density (and thus generally a higher wicking effect) than the other portion in each region 28, 30, it can also work for an effective use of the absorbent core material in each region 28, 30. Further, both the front and rear channels 11 and 13 can work to retain the absorbed body fluids in the inside area of the channels.

Herein, "channel" (or often referred to as "embossed channel") refers to a generally elongated depression formed in at least a portion of an absorbent article. The channel can be formed by compressing, embossing or otherwise modifying or directing the materials of the topsheet and the absorbent core at the channel portion in the manufacture process of absorbent articles.

Typically, the channel is formed by applying a compressive force to both the topsheet and at least a part of the absorbent core toward the backsheet. The material of the topsheet at the channel portion is pushed down into the absorbent core, and the materials of the topsheet and the absorbent core are compressed at and below the bottom of the channel portion. By this operation (which is often called "embossing process"), the channel portion of the absorbent article generally has relatively higher density than the other portion(s) or the surrounding portion(s) of the channel portion.

The channel tends to preferentially diffuse or lead body fluids flow along the direction in which the channel extends. Therefore, the channel is useful to control body fluids flow within the absorbent article thereby preventing body fluids leakage from the absorbent article. The channel also tends to work as a preferential bending axis of the absorbent article. Therefore, the absorbent article may bend at the channel portion such that it provides an improved fit of the absorbent article to the wearer's body. It should be noted that such an improved fit of the absorbent article can also contributes an improvement in preventing body fluids leakage from the absorbent article.

The channel of the present invention can be either continuous or discontinuous. Herein, "discontinuous" means the channel can be separated by a non-channel portion. Herein, "non-channel portion" refers to a portion of absorbent articles where no channel is formed between two component channel portions which are disposed in series. One discontinuous channel includes two or more component channel portions which are separated by a non-channel portion. The distance between the two component channel portions (i.e., the length of the no channel portion) may be changed depending on the product design. The length of the no channel portion can be, for example, from about 0 mm to about 20 mm, from about 2 mm to about 10 mm, or from about 3 mm to about 6 mm.

In one embodiment, channels are formed by applying a uniform (or a single level of) compressive force to the topsheet and the absorbent core toward the backsheet. Alternatively, channels can be formed by applying two or more levels of compressive forces to the topsheet and the absorbent core toward the backsheet thereby forming a "two (or more) stage channel structure".

In the embodiment shown in FIGS. 1 and 2, all the channels 11, 12 and 13 are formed by applying two levels of compressive forces to the topsheet 38 and the absorbent core 42 toward the backsheet 40. The application of the two levels of compressive forces (i.e., higher compression and lower compression) produces two stage depth portions (i.e., "two stage channel structure") in the resulting the channels, i.e., first portion 81 and second portion 82. However, it is not necessary that all the channels be formed the same way or by the same process.

Figure 3:
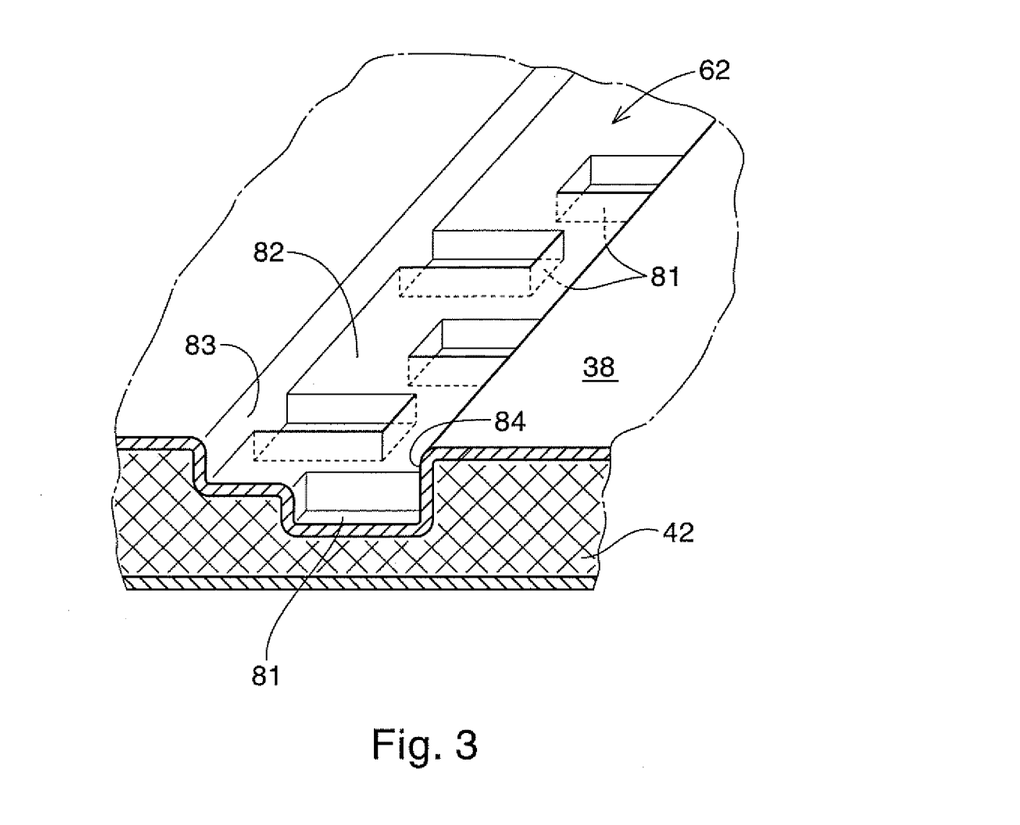
FIG. 3 is a perspective view of an emboss channel formed in the absorbent article shown in FIG. 1.

FIG. 3 is a perspective view of one channel formed in the sanitary napkin 20 shown in FIG. 1. In this embodiment, the channel 62 has two side walls (or channel walls) 83 and 84. The first portions 81 are formed by a higher compression, while the second portion 82 is formed by a lower compression. The absorbent core 42 is more compressed at the portions 81 of higher compression than the portion 82 of lower compression. In the embodiment shown in FIG. 5 (and also FIG. 3), the portions 81 of higher compression form the lowest portions of the channel 62, while the portion 82 of lower compression forms the higher portion in the channel 62. The first portions 81 of higher compression have a higher density than the portion 82 of lower compression as a result of compression force differences. Such a two stage channel structure may provide a better comfort to the wearer's body in use compared with the channel structure which has no stage difference (formed by no compression force differences applied). In addition, since the compression force is more concentrated at the portions 81 of higher compression, the two stage channel structure can also increase the bonding strength between the topsheet 38 and the absorbent core 42 at the portions 81.

The first portions 81 formed by a higher compression extend from one channel wall 83 but does not reach the other channel wall 84. In the embodiment shown in FIG. 3, the shape of the first portions 81 formed by a higher compression is about a rectangular. However, the shape of the first portions 81 can vary depending on the channel design in the sanitary napkin 20. The length, width and depth of the first portions 81 can also vary depending on the channel design in the sanitary napkin 20. Similarly, the shape, the length, width and depth of the second portion 82 can also vary depending on the channel design in the sanitary napkin 20.

The first portions 81 formed by a higher compression are spaced one another. The distance or interval of two adjacent portions 81 can be either consistent or inconsistent. In the embodiment shown in FIG. 1, the distance of two adjacent portions 81 is consistent.

In an alternative embodiment, the first portions 81 may be formed by lower compression, and the second portion 82 may be formed by higher compression. This produces an opposite geographic shape of the channels.

A variety of channel structures which are applicable to the present invention are disclosed in, for example, U.S. Pat. No. 6,563,013 issued to Murota on May 13, 2003. This publication discloses examples of "two stage channel structure" which are applicable to the embodiments of the present invention.

In the embodiment shown in FIG. 3, the first portion 81 formed by a higher compression extends from one channel wall 83 but does not reach the other channel wall 84. This channel structure is referred to as a "stitched channel structure". As an alternative to such stitched channel structures, the first portion 81 formed by a higher compression can extend from one channel wall 83 to the other channel wall 84. Such a structure can be produced by an application of higher and lower compressions alternatively applied along the longitudinal direction of the channel 62. Such channel structures are disclosed in, for example, U.S. Pat. No. 5,795,345 issued to Mizutani et al. on Aug. 18, 1998.

The topsheet 38 is typically compliant, soft feeling, and non-irritating to the wearer's skin. Further, the topsheet 38 is generally at least partially liquid permeable or pervious, permitting body fluids (e.g., menses and/or urine) to readily penetrate through its thickness. A suitable liquid permeable material for the topsheet 38 may be manufactured from a wide range of materials such as woven and nonwoven materials (e.g., a nonwoven web of fibers); polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet 38 includes a nonwoven web, the web may be manufactured by a wide number of known techniques. For example, the web may be spunbonded, carded, wet-laid, melt-blown, hydroentangled, combinations of the above, or the like.

A particularly suitable material for the topsheet 38 includes an apertured formed film. Apertured formed films are preferred for the topsheet 38 because they are pervious to body fluids and, if properly apertured, have a reduced tendency to allow liquids to pass back through and rewet the wearer's skin. Thus, the body surface of the formed film (i.e., the body surface 20A of the sanitary napkin 20) remains dry, thereby reducing body soiling and creating a more comfortable feel for the wearer. One material for use as the topsheet 38 is a macroscopically expanded, three-dimensional formed polyethylene film. One preferred material for the topsheet 38 is available from Tredegar Film Products, Indiana, USA, under Code No. X-15507.

The backsheet 40 is typically at least partially impervious to body fluids and is often manufactured from a thin plastic film, although other flexible materials may also be used. Herein, "flexible" refers to materials which are compliant and will readily conform to the general shape and contours of the human body. The backsheet 40 generally prevents the body fluids absorbed and contained in the absorbent core 42 from wetting articles which contact the absorbent article such as bed sheets, pants, pajamas and undergarments. The backsheet 40 may thus include a woven or nonwoven material, polymeric films such as thermoplastic films of polyethylene or polypropylene, or composite materials such as a film-coated nonwoven material. The backsheet 40 can include a single layer material, or two or more layers of materials. The backsheet 40 preferably has a thickness of from about 0.012 mm (0.5 mil) to about 0.081 mm (3.4 mils). In one embodiment, the backsheet 40 is a single layer polyethylene film. Such a preferred polyethylene film is available from Daedong Co. Ltd., KyungBuk-Do, Korea, under Code No. DNF-0417C-DG.

The backsheet 40 may have a microporous structure which can permit vapors to escape from the absorbent core 42 (often called "breathable backsheet") while still preventing body fluids from passing through the backsheet 40. One suitable microporous polyethylene film is available from Mitsubishi Chemical Corporation, Tokyo, Japan, under Code No. Espoir-N-PSF-B. The backsheet 40 can be embossed to provide a clothlike or any other desired appearance.

The absorbent core 42 is capable of receiving, absorbing or retaining body fluids discharged. The absorbent core 42 is generally compressible, conformable, and non-irritating to the wearer's skin. The absorbent core 42 can be formed by a single layer material or a plurality of layered materials. In one embodiment, the absorbent core 42 includes an acquisition layer or a secondary topsheet which quickly transports discharged body fluids received by the topsheet 38 to other parts of the acquisition layer and the absorbent core 50. The acquisition layer can temporarily hold such fluids until they can be absorbed by the other parts of the absorbent core 50. The distribution function of the acquisition layer is of particular importance in order to more fully utilize the capacity of the absorbent core 50. Thus, while the acquisition layer may comprise a wide variety of absorbent materials, it preferably comprises a fibrous material that can rapidly transport fluid and not collapse upon being wetted so that the acquisition layer can effectively acquire and distribute second and successive fluids.

The absorbent core may include any of a wide variety of liquid-absorbent materials commonly used in absorbent articles, such as comminuted wood pulp, which is generally referred to as airfelt. One suitable absorbent core material is an airfelt material which is available from Weyerhaeuser Company, Washington, USA, under Code No. FR516.

Examples of other suitable absorbent materials for use in the absorbent core include creped cellulose wadding; melt-blown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; absorbent gelling materials; or any equivalent material or combinations of materials, or mixtures of these.

The absorbent core 42 may be manufactured in a wide variety of sizes and shapes. The periphery of the absorbent core 42 thus can take any shape in its top plane view. The core periphery may be any suitable shape, include an oval, a rectangle, an hourglass, and a combination of the oval and rectangle.

In one embodiment, the absorbent core 42 is non-profiled in all the regions 28, 30, 32 so that it has the consistent caliper. The absorbent core 42 may be profiled in the longitudinal direction such that the central region 32 has a basis weight which is greater than that of the front or back end region 28, 30. The absorbent core 42 may be profiled within the central region 32 in the longitudinal direction (and also in the traverse direction if desired) so that the central region 32 has a caliper that is greater than the caliper of the outside of the central region 32. Herein, "profiled" means that one specified portion of a material has a caliper that is greater than that of the other portion to be compared. Herein, calipers of an absorbent core are measured under a pressure of 0.1 psi using a circular comparator foot with a 1 inch (25.4 mm) diameter area. Typically, a profiled portion is formed by increasing the amount of material(s) at the profiled portion of the absorbent core than the other portion such that the profiled portion shows an expanded shape (or appearance) on the body surface 20A compared to the other portion. In the embodiment of FIG. 1, the absorbent core 42 contains an increased amount of material(s) in the central region 32 than the other regions 28 and 30.

The front end region 28 and the rear end region 30 may have the same or similar caliper, while the central region 32 comprises the greatest caliper portion of the sanitary napkin 20 as a result of the profiled structure. The caliper ratio of the profiled portion to the non-profiled portion preferably ranges from about 1.1:1 to about 3:1, and more preferably from about 1.2:1 to about 2:1. In the sanitary napkin 20 shown in FIG. 1, the caliper ratio of the profiled portion to the non-profiled portion is about 1.5:1.

The sanitary napkin 20 can be of any caliper, including relatively thick, relatively thin, or even very thin. The embodiment of the sanitary napkin 20 shown in FIG. 1 is intended to be an example of a relatively thick sanitary napkin having a caliper of about 4 mm in the end regions 28 and 30 and a caliper of about 6 mm in the central region 32. It should be understood, however, when viewing these figures the number of layers of material shown may cause the sanitary napkin 20 to appear much thicker than it actually is, particularly in cross-section.

The topsheet 38, the backsheet 40, and the absorbent core 42 may be assembled in a variety of configurations, sizes and shapes known in the art. Examples of suitable configurations are described in U.S. Pat. Nos. 4,950,264; 5,009,653 issued to Osborn; U.S. Pat. No. 4,425,130 issued to DesMarais; U.S. Pat. Nos. 4,589,876 and 4,687,478 issued to Van Tilburg, and U.S. Pat. No. 5,234,422 issued to Sneller, et al.

The topsheet 38 and the backsheet 40 typically have length and width dimensions generally larger than those of the absorbent core 42. The topsheet 38 and backsheet 40 extend beyond the edges of the absorbent core 42, and are joined together to form a pair of central side flaps 52. These topsheet 38 and backsheet 40 can be joined any means (e.g., an adhesive) known in the art.

The central side flaps 52 can be in any suitable configuration and shape known in the art. Examples of suitable flaps are described in U.S. Pat. No. 5,389,094 issued to Lavash, et al. on Feb. 14, 1995; and U.S. Pat. No. 5,558,663 issued to Weinberger, et al. on Sep. 24, 1996.

In the embodiment shown in FIG. 1, the central side flaps 52 are integral with the main body portion 25 of the sanitary napkin 20 (i.e., these flaps 52 comprise integral extensions of the topsheet 38 and the backsheet 40 from the main body portion 25). Alternatively, these flaps can be formed by separate materials from the topsheet 38 and the backsheet 40, which are joined to the main body portion 25 of the sanitary napkin 20 in any suitable manner. In that event, the flaps are each joined to (or associated with) the main body portion 25 along a juncture, typically a longitudinally-oriented (or "longitudinal") juncture. Examples of suitable side flap structures are described in, for example, U.S. Pat. No. 5,389,094 issued to Lavash, et al. on Feb. 14, 1995; and U.S. Pat. No. 5,558,663 issued to Weinberger, et al. on Sep. 24, 1996.

Sanitary napkin 20 may be attached to the wearer's panties or undergarment through adhesive fasteners as known in the art. The fasteners comprise a plurality of patches of adhesive which are adhered to the garment surface 20B of the backsheet 40 of the sanitary napkin 20. Those fasteners include one or two (or more if desired) adhesive patches (i.e., panty fastening adhesive) that are disposed on the main body portion 25 of the sanitary napkin 20 such that the sanitary napkin 20 can adhere to the crotch area of the wearer's undergarment to keep the sanitary napkin 20 in place. Those fasteners also include a pair of additional adhesive patches (i.e., flap adhesives) that are disposed on the garment surface 20B of the central side flaps 52 of the sanitary napkin 20 to adhere to the undersides of the wearer's undergarment during use and to keep the napkin 20 in place to improve fit. Examples of suitable adhesive fastener structures including release strips are described in, for example, U.S. Pat. No. 6,074,376 issued to Mills on Jun. 13, 2000.

Figure 4:
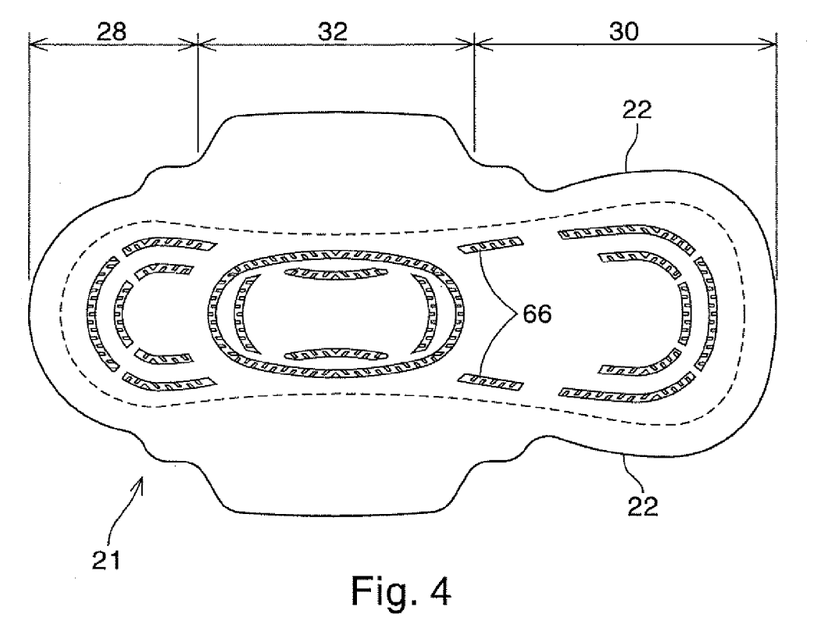
FIG. 4 is a top plane view of another preferred embodiment of the absorbent article of the present invention.

FIG. 4 is a top plane view of a sanitary napkin 21 which is another embodiment of the invention. Compared with the embodiment of FIG. 1, the sanitary napkin 21 is elongated and asymmetrically shaped such that the rear end region 30 has greater width and length than the front end region 28. The sanitary napkin 21 further includes a pair of longitudinal channels 66 at the transition area of the central region 32 and the rear end region 30. The other portions are similar to those of the sanitary napkin shown in FIG. 1.

The widths of the front and rear end regions 28, 30 are defined by the traverse distance between the longitudinal edges 22 of the sanitary napkin 20. The ratio of the widths of the rear end region 30 to the front end region 28 can range from between about 1:1 and about 2.5:1. The ratio of the widths of the rear end region 30 to the front end region 28 may also be about 1.2:1. The ratio of the longitudinal lengths of the front end region 28 to the central region 32 is from about 1:1 to about 1:4, and the ratio of the longitudinal lengths of the central region 32 to the rear end region 30 is from about 1:0.5 to about 1:3. In the embodiment shown in FIG. 4, the ratio of the longitudinal lengths of the front end region 28 to the central region 32 and the rear end region 30 is about 1:2.0:1.9.

Figure 5:
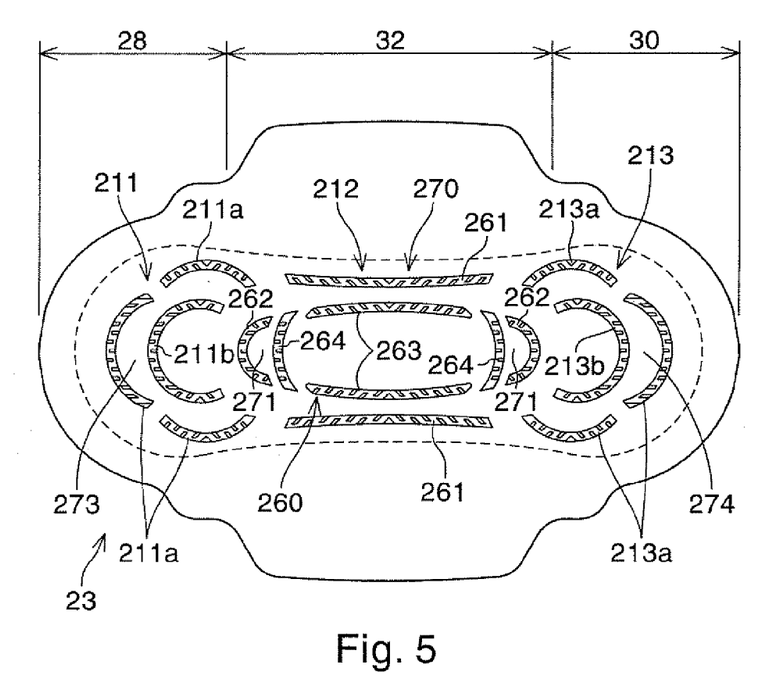
FIG. 5 is a top plane view of yet another preferred embodiment of the absorbent article of the present invention.

FIG. 5 is a top plane view of a sanitary napkin 23 which is yet another embodiment of the invention. Compared with the embodiment of FIG. 1, the sanitary napkin 23 has different channel designs, i.e., front channels 211, central channels 212, and rear channels 213. The central channels 212 include a pair of inwardly convex longitudinal channels 261 and a pair of outwardly convex traverse channels 262. The central channels 212 further include a pair of outwardly convex longitudinal channels 263 and a pair of outwardly convex traverse channels 264. The pair of outwardly convex traverse channels 262 and the pair of outwardly convex longitudinal channels 263 form an oval channel 260 in the central region 32. The sanitary napkin 23 further includes a reinforcing structure 270 disposed within the central region 32. The reinforcing structure 270 includes two traverse reinforcing elements 271 each of which is formed by the two traverse channels 262 and 264.

The front channels 211 include four outwardly convex arc channels 211a and 211b, while the rear channels 213 include four outwardly convex arc channels 213a and 213b. It should be noted that the front channels 211 and the rear channels 213 are optional but they are often desirable and can provide an outwardly convex arc like reinforcing element 273, 274 in each region 28 and 30 as shown in FIG. 5. I.e., the sanitary napkin 23 further includes the outwardly convex arc like reinforcing element 273 which is formed by the arc channels 211a and 211b formed in the front end region 28, and the outwardly convex arc like reinforcing element 274 which is formed by the arc channels 213a and 213b formed in the rear end region 30.

Test Method

This method describes the procedure that is used for determining a compressive modulus of a sample member (i.e., an absorbent article) against an externally applied compression. In general, this procedure involves a measurement of rate of a force which is generated when a sample member is pushed down by a predetermined probe at a probe contacting area of the sample member. In the measurement, the compressive modulus is measured as a rate of a pressure kPa (kilopascal) required to cause a unit strain when a sample member is continuously pushed down at 75% of the original thickness (i.e., at a strain of 25%).

The test apparatus comprises a horizontal, smooth and rigid plate and a vertically movable bar which is positioned above the horizontal plate. The plate should be made of stainless steel or other rigid, non-corrosive metal. A preferred plate is a stainless steel plate.

A sample member is fixed on the horizontal plate. A probe which has a circular flat top of an area about 2 cm$^2$ is attached to the bar so that the top of the probe is positioned slightly above the top surface of the sample member. The portion of the sample member where the top of the probe contacts is called as "probe contacting area". The probe is connected to a pressure sensor which measures, through the probe, the resilient pressure generated from the member at the probe contacting area.

The bar moves downwardly at a cross-head speed of about 0.01 cm/sec until the thickness becomes 65% of the original thickness (i.e., a strain of 45%). The resilient force which is measured by the sensor is continuously recorded by a recorder (e.g., a computer system). The original thickness of the sample member is determined by the distance between the top of the probe and the horizontal plate under the pressure of 0.049 kPa. The rate of a pressure (kPa)) required to cause a strain of 1% at 75% of the original thickness (i.e., a strain of 25%) is calculated by the system automatically. This measurement is repeated at least 3 times on different sample members. The average value of the measurements is defined as the compressive modulus.

The test apparatus for the measurements is available from Kato Tech Co., Kyoto, Japan, under the Code No. "KES G-5".

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a front end region, a rear end region, a central region disposed between the front and rear end regions, a fluids source area, and a transverse axis and a longitudinal axis, the absorbent article comprising:
   a topsheet;
   a backsheet;
   an absorbent core disposed between the topsheet and the backsheet; and
   a reinforcing structure, the reinforcing structure including two or more traverse reinforcing elements which are formed by two traverse channels;
   wherein each of the two or more traverse reinforcing elements formed by two traverse channels cross a longitudinal centerline and form inwardly convex ellipses, wherein each of the respective two traverse channels forming one of the two or more traverse reinforcing elements cross the longitudinal axis, and
   wherein at least one of the two or more traverse reinforcing elements is not located in the central region.

2. The absorbent article of the claim 1, wherein the fluids source area has a compressive modulus and at least one of the traverse reinforcing elements has a compressive modulus which is higher than the compressive modulus of the fluids source area.

3. The absorbent article of the claim 1, wherein at least one of the traverse reinforcing elements has a compressive modulus of about 2 psi to about 50 psi (about 13.8 kPa to about 344.7 kPa).

4. The absorbent article of the claim 1, wherein the reinforcing structure further includes at least one longitudinal reinforcing element which is formed by two longitudinal channels.

5. The absorbent article of the claim 4, wherein the at least one longitudinal reinforcing element includes a pair of longitudinal reinforcing elements each of which is formed by the two longitudinal channels.

6. The absorbent article of the claim 1, wherein the traverse reinforcing elements have a traverse length of about 20% to about 100% of the minimum width of the absorbent core.

7. The absorbent article of the claim 1, wherein the absorbent core includes about 100 weight % of cellulose fibers.

8. The absorbent article of the claim 1, wherein the absorbent core is profiled in the longitudinal direction such that a central region has a basis weight which is greater than that of the front or back end region.

9. The absorbent article of the claim 1, wherein each of the two channels has higher compressive portions and lower compressive portions which are alternatively repeated along the longitudinal direction of the channel.

10. The absorbent article of the claim 1, wherein the absorbent article is a sanitary napkin, pantiliner, or incontinence article.

* * * * *